(12) United States Patent
McKenzie et al.

(10) Patent No.: US 9,373,167 B1
(45) Date of Patent: Jun. 21, 2016

(54) HETEROGENEOUS RENDERING

(71) Applicant: Intrinsic Medical Imaging LLC, Bloomfield Hills, MI (US)

(72) Inventors: Lee R. McKenzie, Howell, MI (US); Amy Steffek, Birmingham, MI (US)

(73) Assignee: Intrinsic Medical Imaging, LLC, Bloomfield Hills, MI (US)

( * ) Notice: Subject to any disclaimer, the term of this patent is extended or adjusted under 35 U.S.C. 154(b) by 0 days.

(21) Appl. No.: 14/054,466

(22) Filed: Oct. 15, 2013

Related U.S. Application Data

(60) Provisional application No. 61/713,849, filed on Oct. 15, 2012.

(51) Int. Cl.
*G06T 7/00* (2006.01)
*G06T 15/08* (2011.01)

(52) U.S. Cl.
CPC ............... *G06T 7/0012* (2013.01); *G06T 15/08* (2013.01)

(58) Field of Classification Search
CPC ............ G06T 5/50; G06T 2207/10081; G06T 2207/10116; G06T 2207/10072; G06T 3/4053; G06T 15/08; G06T 2210/41; G06T 2207/30101; G06T 7/0081; G06T 2207/30028; G06T 7/0012; G06T 11/008; G06T 17/00; G06T 2200/04; G06T 2207/30096; G06T 2207/30104; G06T 2207/30004; G06T 15/005; G06T 2207/10088; G06T 15/06; G06T 2207/20148; G06T 15/00; H04N 1/3935; A61B 6/466; A61B 8/483; A61B 6/5205; Y10S 378/901

USPC .......................................................... 345/424
See application file for complete search history.

(56) References Cited

U.S. PATENT DOCUMENTS

| | | | |
|---|---|---|---|
| 2005/0119550 A1* | 6/2005 | Serra et al. ..................... | 600/407 |
| 2005/0276455 A1* | 12/2005 | Fidrich et al. .................. | 382/128 |
| 2006/0020202 A1* | 1/2006 | Mathew et al. ................ | 600/437 |
| 2007/0024617 A1* | 2/2007 | Poole ............................. | 345/424 |

OTHER PUBLICATIONS

Ruijters, Dynamic Resolution in GPU-Accelerated Volume Rendering to Autostereoscopic Multiview Lenticular Displays, EURASIP Journal on Advances in Signal Processing, vol. 2009, Article ID 843753, 8 pages, pp. 1-8.*

* cited by examiner

*Primary Examiner* — Haixia Du
(74) *Attorney, Agent, or Firm* — David H. Judson

(57) ABSTRACT

A machine-implemented display method that, with respect to a volume dataset being rendered, enables a user to navigate to any position in space and look in any direction. Preferably, the volume dataset is derived from a computer tomography (CT) or magnetic resonance imaging (MRI) scan. With the described approach, the user can see details within the dataset that are not available using conventional visualization approaches. The freedom-of-motion capability allows the user to go to places (positions) within the volume rendering that are not otherwise possible using conventional "orbit" and "zoom" display techniques. Thus, for example, using the described approach, the display image enables a user to travel inside physical structures (e.g., a patient's heart, brain, arteries, and the like). In this approach, a display image includes information visually representing an amount of difference between a current pixel and its neighbor pixels.

9 Claims, 5 Drawing Sheets

HETEROGENEOUS RENDERING

BACKGROUND

Medical imaging is the technique used to create images of the human body or parts thereof for clinical purposes (medical procedures that seek to reveal, to diagnose or to examine disease) or medical science (including the study of normal anatomy and physiology). Computer tomography (CT) and magnetic resonance imaging (MRI) are two of the most common approaches. These techniques generate a set of individual 2D images that can be displayed in a 3D visualization as a "volume dataset."

Volume rendering in particular is a process by which data composed of individual slices or images that are captured from an X-ray CT scanner or MRI scanner are used to generate an image from a unique position and direction in 3D space. Traditionally, this process involves rays being fired from unique positions and directions in the dataset and examining each pixel along the trajectory. Using a previously-determined accumulation function, each pixel is blended into a final grayscale or color value, and collected to form an image.

In the fields of Radiology and Interventional Cardiology, a particularly important aspect of diagnosing and treating the patient is being able to accurately image the arteries or vessels of the body. Typically, the patient will be given an X-ray CT scan, which creates a collection of consecutive image slices that form a volume of patient data when stacked, or rendered, electronically. Several known rendering methods that allow CT data to be viewed have emerged over the years. One of the most straight-forward methods, Multi-Planar Reconstruction (MPR), creates a view aligned plane that cuts through the volume data, often at an oblique angle. Using the MPR view, the clinician can adjust the position and orientation of this plane, so as to be able to see different views of the scanned anatomy as a 2D, grayscale image.

In the field of Interventional Cardiology, the MPR plane is used to create a cross-sectional view of the artery. This cross-sectional, or lumenal, view allows the clinician to assess the presence and severity of characteristics common to cardiovascular disease, such as stenosis (lumenal narrowing) and plaque accumulation in the arterial wall.

The challenge to interpreting a grayscale cross-sectional view of the artery, is reliably determining what constitutes the open area of the artery, or lumen, versus the arterial wall. This visual ambiguity leads to widely different interpretations of the same MPR image. The currently accepted margin of error for this type of reading is 20-40%, due to the subjective nature of the interpretation. Furthermore, increasing importance is being placed on the ability to accurately assess plaque volume and composition. This has proven inherently difficult as these materials differ only subtly, or not at all, when viewed in the grayscale cross-section.

Current MPR rendering methods employ a strategy based on voxel value for data reconstruction. The grayscale values of the voxels map to specific Hounsfield Units (HUs), which are a measure of radio-density. In an attempt to overcome the shortcomings of grayscale MPR, colorized versions have been developed where Hounsfield Unit ranges that are consistent with specific tissues, structures, or materials are assigned colors. For example, 100-200 HUs, a range that is consistent with the radio-density of arterial wall tissue, could be assigned the color green, plaque might be characterized as 200-300 HUs and colored blue, while contrast fluid within the lumen might be characterized as 500-1000 HUs and colored red. Although the goal of colorizing the MPR view was to not only alleviate the subjectivity of reading the grayscale images, but also to be able to more specifically characterize the composition of the arterial cross section, it has proven unreliable. Studies have shown that HU ranges can have significant inter- and intra-scan variability based on many factors, including, but not limited to: patient body mass, scanning protocol variations, the amount of contrast used, timing of the contrast, strength of radiation of a particular scan, type of plaque present in the artery, etc. These factors make the task of assigning an accurate universal color map that is based on Hounsfield Units an ill-posed problem. As a result, the traditional grayscale MPR view representing original voxel data remains the preferred viewing method.

BRIEF SUMMARY

The disclosed subject matter, referred to herein as "heterogeneous rendering," uses an approach to pixel or voxel value rendering that can be used as an additional tool for image analysis of 2D and 3D images. The motivation for the approach is as follows. If one thinks of a lumen, the open area of the artery, as well as the pixels in the cross section of the lumen, one can imagine that the neighboring pixels, if also part of the lumen, should be a similar value (e.g., in Hounsfield Units). Conversely, if one of the neighboring voxels is part of the arterial wall, one should expect a dissimilar HU value for that pixel. Thus, rather than relying upon the original value, which can vary from scan to scan, and within the same scan, heterogeneous rendering according to this disclosure preferably draws information from an amount of difference present between a current voxel and its neighbors and visualizes this difference. As a result, the approach creates a view that is not prone to image construction variation. The visualization of the amount of difference present between the current voxel and its neighbors, or in other words the voxels heterogeneity, provides a significant enhancement over known prior schemes.

The foregoing has outlined some of the more pertinent features of the disclosed subject matter. These features should be construed to be merely illustrative. Many other beneficial results can be attained by applying the disclosed invention in a different manner or by modifying the subject matter as will be described.

BRIEF DESCRIPTION OF THE DRAWINGS

For a more complete understanding of the subject matter and the advantages thereof, reference is now made to the following descriptions taken in conjunction with the accompanying drawings, in which.

DETAILED DESCRIPTION

Figure 1:
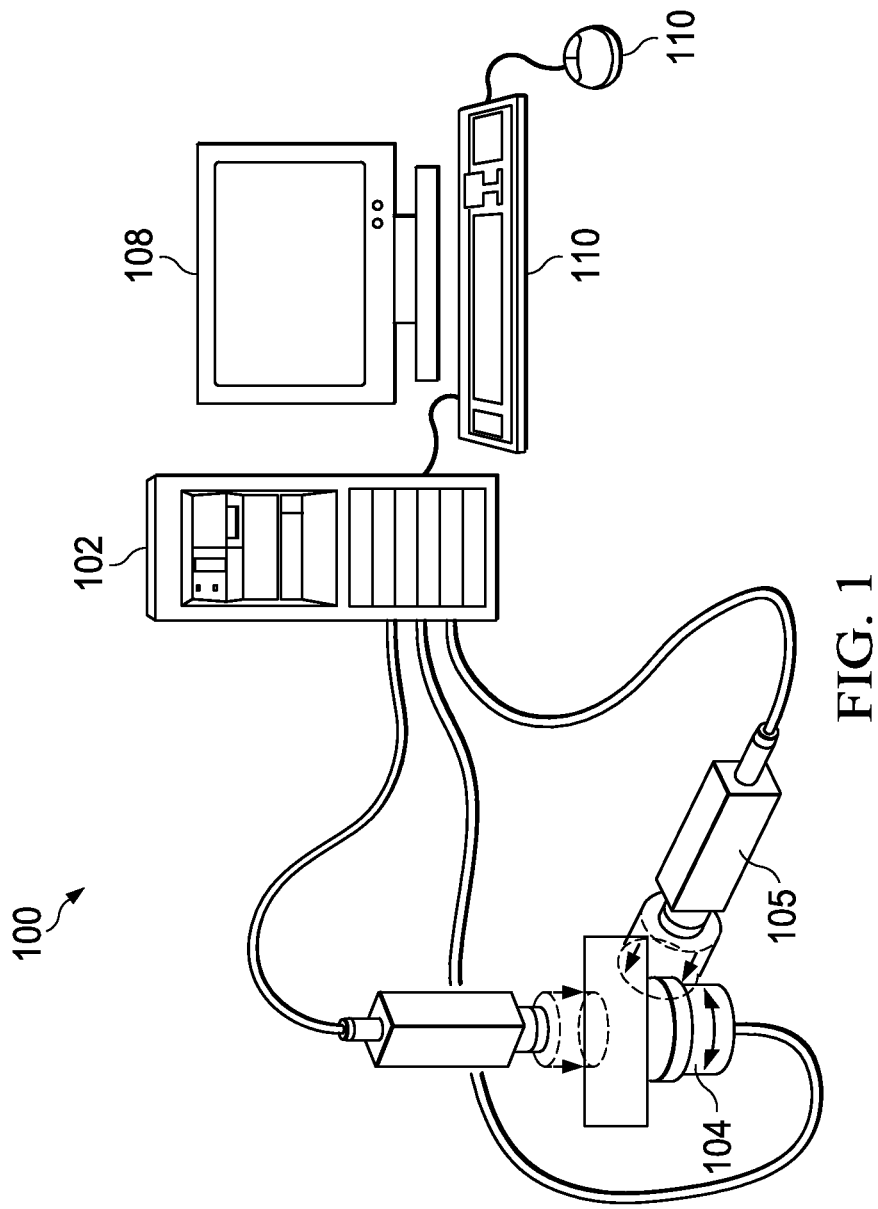
FIG. 1 illustrates a computer system coupled to a medical imaging system.

As illustrated in FIG. 1, a system 100 in which the subject matter herein is implemented comprises a computer system 102 having a display monitor 108, and one or more input devices 110 such as a keyboard, a pointing device, or the like. The computer system 102 is illustrated as a desktop workstation, but this is not a limitation, as the system may be implemented in a laptop or notebook computer, a wireless computing device (such as an iPad), or any other computing machine that includes a display. The techniques of this disclosure are not limited to any particular type of computing device, system or architecture, and one or more of the elements of the machine may be located in different locations. Thus, for example, the display monitor may be positioned remotely from other components. For convenience of illustration only, the computer system 102 is shown as receiving inputs from a pair of imaging devices 105 that are associated with a support 104. The support 104 rotates or reciprocates relative to the imaging devices 105 to generate a set of individual 2D images of an object being scanned. Typically, the support 104 has associated mechanical elements, hydraulic elements and/or electronic elements (not shown) that control the position or rotational speed thereof. The support may be under computer control. Likewise, the one or more imaging devices 105 include associated optical elements, mechanical elements, and/or other control elements that control the position and operation of the device.

Typically, an object to be imaged (e.g., a human body, or some part thereof) is located on the support 104. The support may be fixed, in which case the imaging devices 105 rotate or reciprocate with respect thereto. One of ordinary skill in the art will appreciate that the support 104 and imaging devices 105 represent conventional medical imaging systems such as computer tomography (CT), magnetic resonance imaging (MRI), or the like. Typically, such systems are external to the imaging system of this disclosure, although the imaging techniques herein may be implemented natively within such known imaging systems. The 2D images comprising a particular scan typically conform to a standard digital data format (e.g., DICOM) and are received by the computer system 102 in any convenient manner, e.g., a CD, DVD, USB stick, hard drive, network drive, PACS (a medical CT library), or the like. Of course, the computer system 102 may be network-accessible, in which case the digital data comprising the volume data may be received over a communication network, such as any Internet Protocol (IP)-based network, a wireline network, a wireless network, or the like.

As noted above, this disclosure provides a display method, preferably implemented in a computer, such as a workstation as shown in FIG. 1. More generally, the method is implemented using one or more computing-related entities (systems, machines, processes, programs, libraries, functions, code, or the like) that facilitate or provide the inventive functionality. In a representative but non-limiting implementation, the display methods described herein are implemented in a machine comprising a CPU (central processing unit), such as any Intel- or AMD-based chip, computer memory, such as RAM (at least 1 GB), a hard drive (at least 8 GB), and a CD-drive (preferably 24-48x). The machine software includes an operating system (e.g., Windows XP, Windows Vista, Windows 7, any Apple OS, either 32 bit or 64 bit), and generic support applications. If the process is implemented in a graphics processor, preferably the machine comprises a graphics processing unit (GPU) such as the AMD Radeon Series 4850 or equivalent (preferably at least DirectX 9-compliant and Pixel Shader 3.0-compliant).

Figure 2:
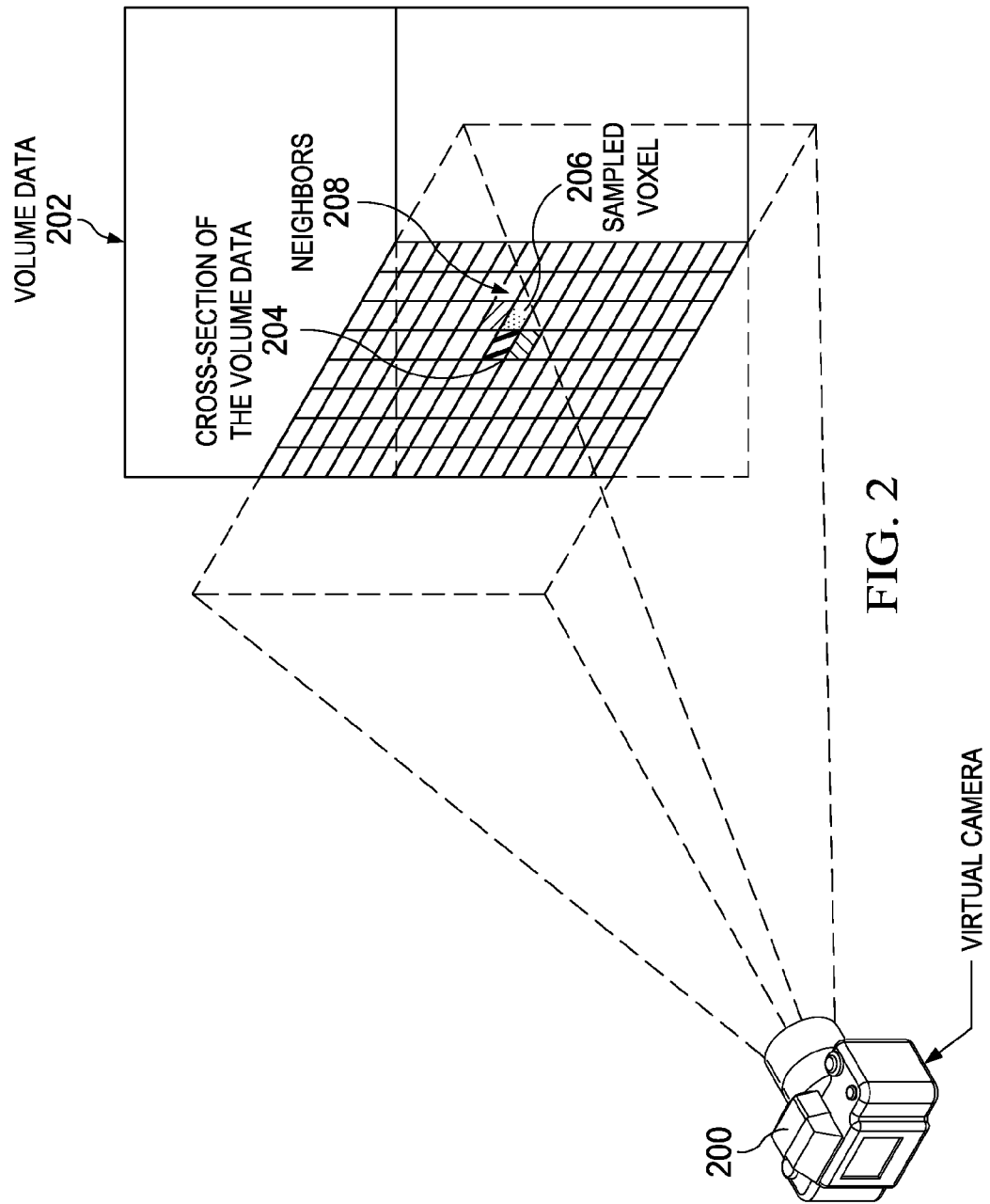
FIG. 2 illustrates 3D virtual camera geometry used in this technique.

A preferred approach to implementing heterogeneous multi-planar reconstruction is now described. Referring now to FIG. 2, multi-planar reconstruction (MPR) is a method where a virtual camera 200 intersects the volume of data 202 centered at a particular position. A user is able to adjust the position and the orientation of the virtual camera in order to view a particular cross-section of the volume dataset. As shown in FIG. 2, the cross-section is often an oblique arbitrary slice 204 through the volume data. The voxels that intersect this slice are sampled and rendered to the screen, usually with some form of interpolation, because the slice may intersect the voxel away from its center. Rather than sampling and rendering the voxels directly, a heterogeneous rendering according to this disclosure samples a voxel 206 intersecting the slice along with the voxel's neighboring voxels 208.

Figure 3:
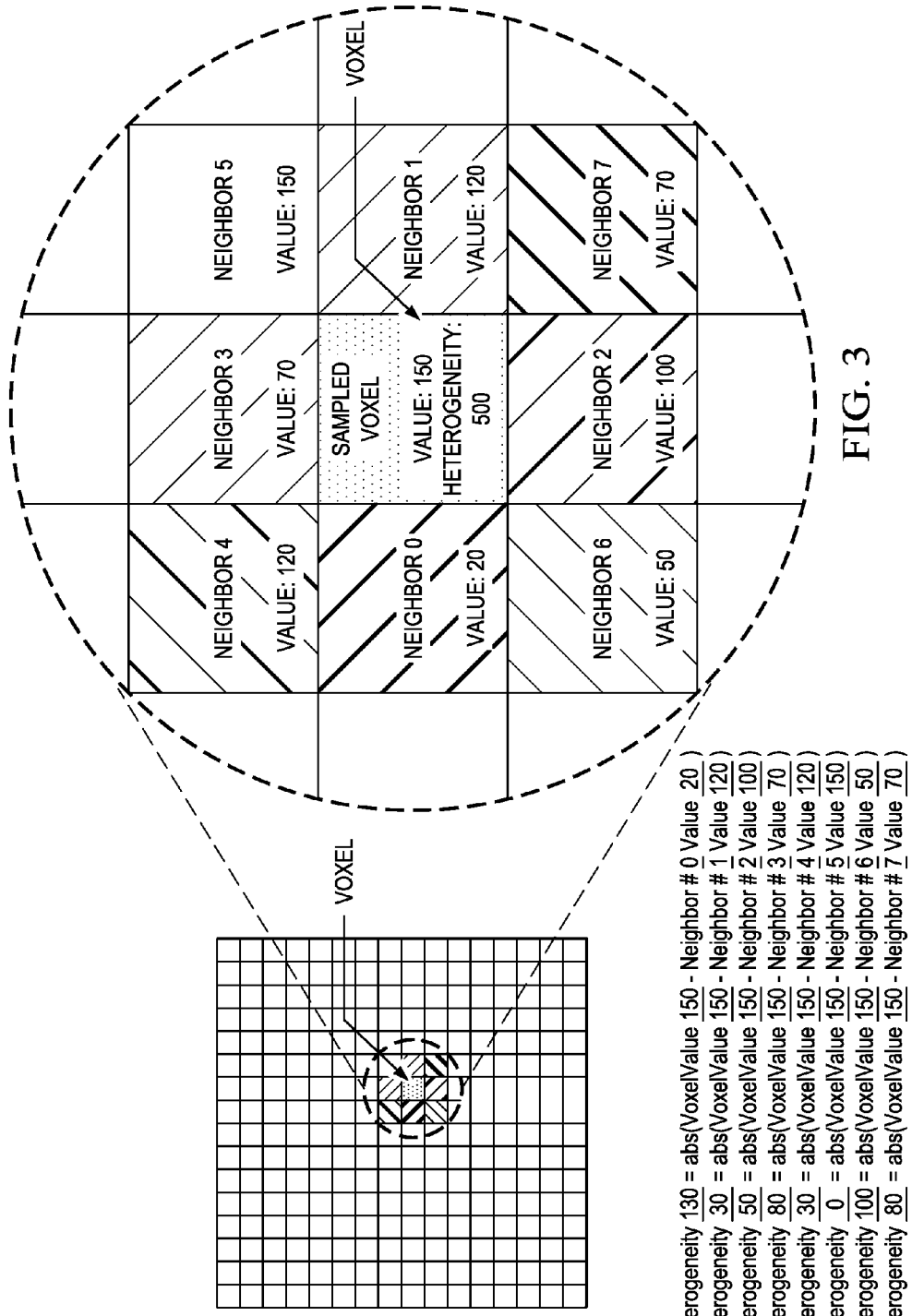
FIG. 3 illustrates a heterogeneity calculation according to this disclosure.
Figure 4:
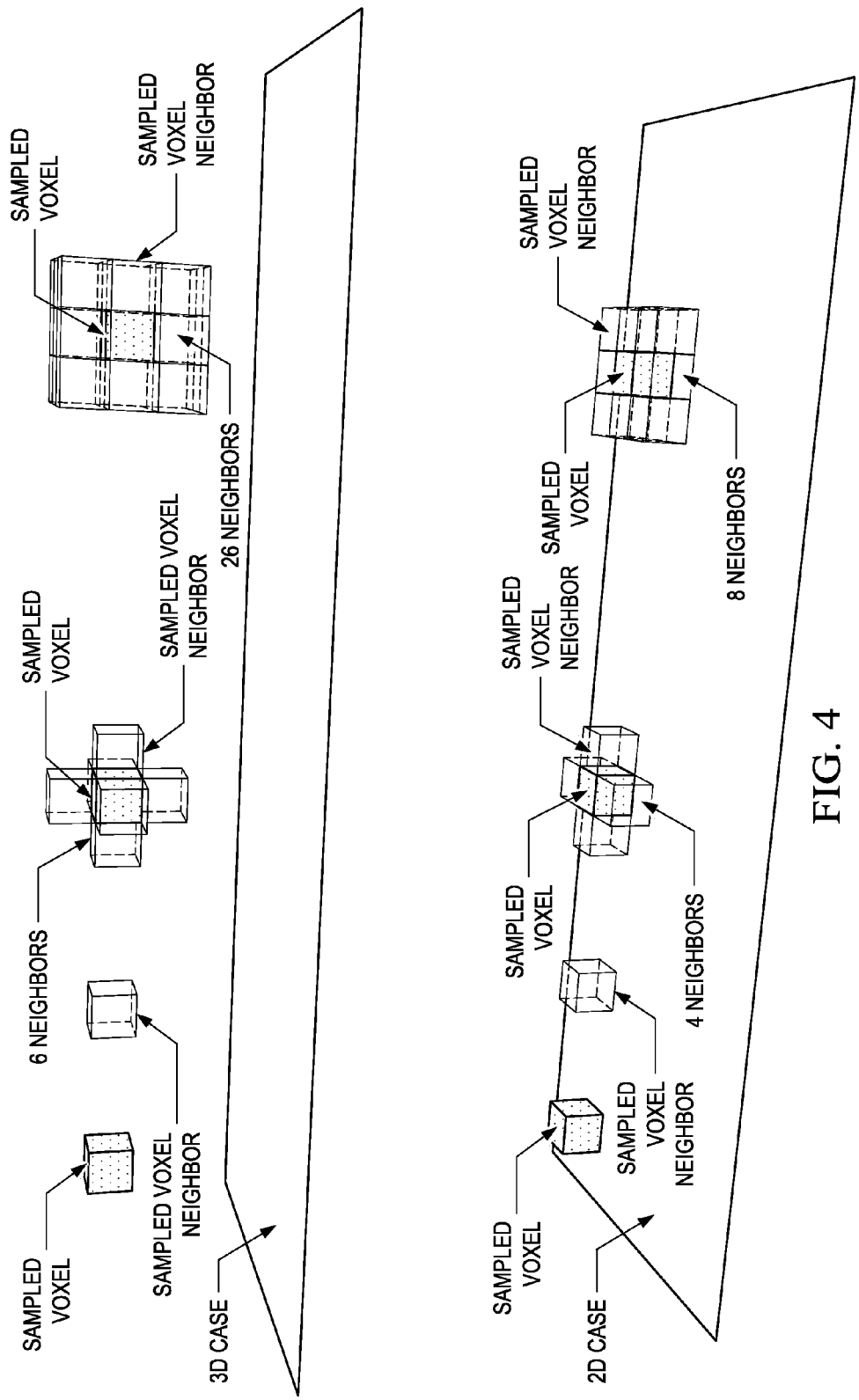
FIG. 4 illustrates various heterogeneity calculations using different sets of neighbor voxels.

FIG. 3 illustrates this heterogeneous rendering technique in more detail. The approach described herein performs a calculation to attain the voxel's heterogeneity, and then visualizes this value instead of the voxel's original value. As shown in FIG. 3, preferably the heterogeneity for any voxel is calculated by taking the sum of the difference between a sampled voxel and its neighboring voxels, where the number of neighbor voxels can range from 1 to 26 as illustrated in FIG. 3 for any sampling of the volume dataset. Preferably, the unsigned heterogeneity for any voxel is calculated by taking the absolute value of the sum of the difference between a sampled voxel and its neighboring voxels, instead of the signed value, where the number of neighbor voxels can range from 1 to 26 as illustrated in FIG. 4 for any sampling of the volume dataset. FIG. 4 illustrates the one neighbor, four neighbor, six neighbor and twenty-six neighbor scenarios. The number of neighbors used for a particular voxel calculation may vary across the rendering, or it may be a uniform calculation.

Unsigned heterogeneity is a quantity that describes a difference of a voxel in relation to its neighbors, whether positive or negative. This is different than signed heterogeneity, which preferably describes a quantity that relates to the positive or negative difference of a voxel value as compared to its neighbors. Unsigned heterogeneity can be used as an alternative to or in combination with signed heterogeneity to obtain a more precise visualization.

A preferred approach to implementing heterogeneous maximum intensity projection is now described. To implement the approach herein, a user uses a virtual camera in the same way as for MPR, but instead of using a single slice of camera aligned data, the heterogeneous rendering approach herein uses multiple slices to render a view of the volume. For each pixel in the output image, the algorithm steps through multiple slices until a predefined thickness is reached and examines each sampled voxel to determine if it is the maximally intense or brightest voxel. If this voxel is the brightest, preferably it is stored for output to the screen. Preferably, the heterogeneous rendering algorithm renders a volume of data by sampling along a ray aligned with the camera for each pixel in the output image, and storing a maximally-intense voxel encountered in the volume for output to the display. Instead of sampling and examining the voxel values for maximum intensity directly, heterogeneous rendering preferably samples the voxel along with the voxel's neighboring voxels, as has been described. It then performs a calculation to attain the voxel's heterogeneity, and examines this value for maximum intensity instead of the voxel's original value. As described, preferably the heterogeneity for any voxel is calculated by taking the sum of the difference between a sampled voxel and its neighboring voxels, where the number of neighbor voxels can range from 1 to 26 as illustrated in FIG. 4 for any sampling of the volume dataset.

A preferred approach to implementing heterogeneous volume rendering is now described. The approach uses a virtual camera, possibly using the technique described in U.S. Pat. No. 8,244,018, the disclosure of which is incorporated herein by reference. The camera may be placed interior to the dataset, or exterior to it. In one embodiment, rays are fired from the camera location outward into the dataset. As the ray walks through the volume dataset it samples the voxels at locations in the dataset. Rays could walk in a linear fashion with a fixed step size, or a non-linear one with a dynamic step. The value that is sampled from the volume can be used to look up a color stored in a table for output to the display. Alternatively, the value may be used to adjust the step dynamically or even be visualized directly. In a preferred embodiment, the value is retrieved from a color table or in some other manner is accumulated at each step of the ray, and the ray will continue to walk the dataset until a predetermined condition is met. Some examples of such a condition are, when the depth is greater than max depth, or when the step count is greater than the allowed number of steps. Once finished, the accumulated color will be presented to the screen.

To implement heterogeneous volume rendering, instead of sampling and examining the voxel values and using them to look up a color directly, heterogeneous rendering preferably samples the voxel along with the voxel's neighboring voxels. It then performs a calculation to attain the voxel's heterogeneity, and uses this value to look up a color in the table instead of the voxel's original value. Note that this value could also drive a dynamic step calculation instead of looking up a color. Again, it should be noted that the calculation of the voxel heterogeneity preferably is the same for all cases and is calculated by taking the sum of the difference between a sampled voxel and its neighboring voxels, where the number of neighbor voxels can range from 1 to 26 as illustrated in FIG. 4 for any sampling of the volume dataset.

Figure 5:
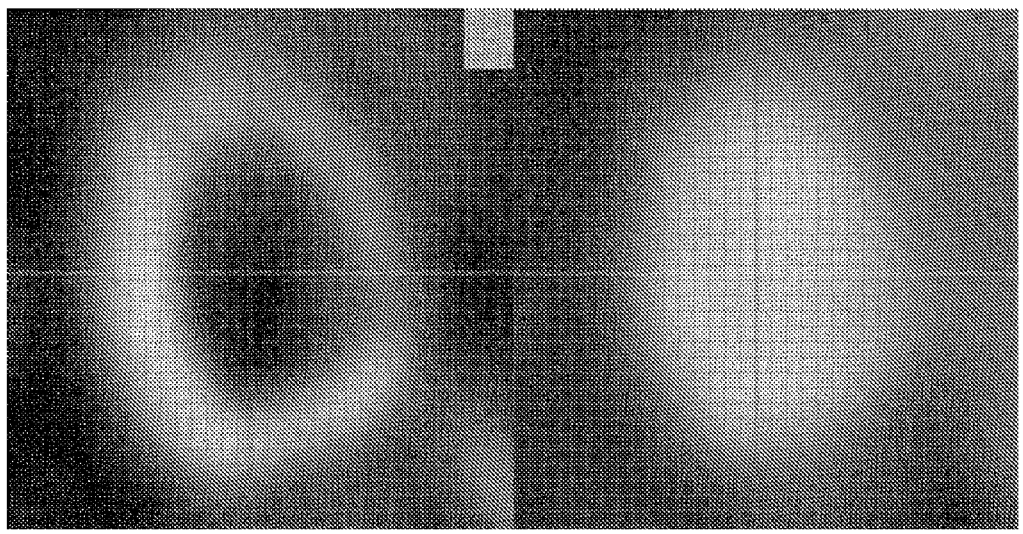
FIG. 5 illustrates side-by-side views of a same artery that has no apparent plaque, wherein the left side illustrates the view using the heterogeneous rendering technique of this disclosure, and wherein the right side illustrates a conventional view using MPR.
Figure 6:
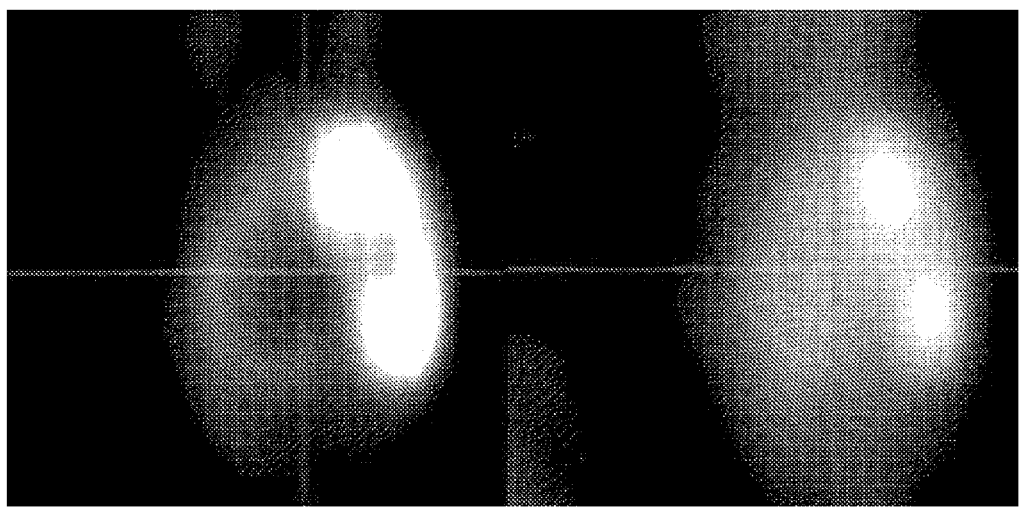
FIG. 6 illustrates side-by-side views of a same artery with plaque, wherein the left side illustrates the view using the heterogeneous rendering technique of this disclosure, and wherein the right side illustrates a conventional view using MPR.

FIGS. 5 and 6 are views showing the benefits of heterogeneous rendering as described herein. In particular, FIG. 4 illustrates side-by-side views of a same artery that has no apparent plaque, wherein the left side illustrates the view using the heterogeneous rendering technique of this disclosure, and wherein the right side illustrates a conventional view using MPR. FIG. 5 illustrates side-by-side views of a same artery with plaque, wherein the left side illustrates the view using the heterogeneous rendering technique of this disclosure, and wherein the right side illustrates a conventional view using MPR. In both cases, the goal is to be able to determine the amount of stenosis of the artery. To be able to determine the amount of stenosis, the boundary of the arterial lumen must be discernible. Using traditional MPR, the boundary of the arterial lumen is quite difficult to discern due to the many shades of grey providing little visual contrast. The benefits of heterogeneous rendering are easily seen in these examples.

For computational efficiency, the above-described approach may be implemented using a GPU so that many pixels can be processed in parallel. In the alternative, a multi-core CPU can be used to facilitate the parallel processing.

More generally, the techniques described herein are provided using a set of one or more computing-related entities (systems, machines, processes, programs, libraries, functions, or the like) that together facilitate or provide the described functionality described above. In a typical implementation, a representative machine on which the software executes comprises commodity hardware, an operating system, an application runtime environment, and a set of applications or processes and associated data, that provide the functionality of a given system or subsystem. As described, the functionality may be implemented in a standalone machine, or across a distributed set of machines.

While certain aspects or features have been described in the context of a computer-based method or process, this is not a limitation of the invention. Moreover, such computer-based methods may be implemented in an apparatus or system for performing the described operations, or as an adjunct to other dental restoration equipment, devices or systems. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including optical disks, CD-ROMs, and magnetic-optical disks, read-only memories (ROMs), random access memories (RAMs), magnetic or optical cards, or any type of media suitable for storing electronic instructions, and each coupled to a computer system bus. The described functionality may also be implemented in firmware, in an ASIC, or in any other known or developed processor-controlled device.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature, structure, or characteristic.

While given components of the system have been described separately, one of ordinary skill will appreciate that some of the functions may be combined or shared in given systems, machines, devices, processes, instructions, program sequences, code portions, and the like.

The volume dataset may be generated from any data source. It is not required that the volume dataset be CT or MRI data, or that the data itself be medical imaging data. The techniques herein may be used within any volume dataset irrespective of content.

A tangible (non-transitory) machine-readable medium stores the computer program that performs the dynamic rendering resolution and dynamic per-pixel ray tracing during the process of rendering the volume dataset on the display. The program receives the volume dataset and renders the virtual camera construct (which lives inside the machine).

Having described our invention, what we now claim is as follows.

The invention claimed is:

1. An article comprising a tangible, non-transitory machine-readable medium that stores a program, the program being executed by a machine having a hardware component to perform a method, the method comprising:
   associating multiple colors in a color map to respective ranges of volumetric density measures;
   receiving a volume dataset defining a volume; and
   rendering a view of a dataset, wherein a voxel visualized in the view has a value that is dependent upon a heterogeneity of the voxel at a sample location, the heterogeneity being calculated by taking a sum of a difference between a sampled voxel and its neighbor voxels;

the voxel having a color that is a selected one of the multiple colors, the color being selected by using the value to perform a lookup into the color map;

wherein the view comprises multiple voxels, wherein the number of neighbor voxels used to determine the values of the voxels varies across the view.

2. The article as described in claim 1 wherein a number of neighbor voxels is between 1 and 26.

3. The article as described in claim 1 wherein the heterogeneity is an unsigned heterogeneity that is calculated by taking a sum of absolute value of the difference between a sampled voxel and its neighbor voxels.

4. The article as described in claim 1 wherein the value being visualized is the heterogeneity itself.

5. The article as described in claim 1 wherein the value being visualized is a result of a calculation where heterogeneity is a variable.

6. Apparatus, comprising:

a display;

a processor; and computer memory holding computer program instructions executed by the processor, the computer program instructions comprising:

program code operative to associate multiple colors in a color map to respective ranges of volumetric density measures;

program code operative to receive a volume dataset defining a volume; and program code operative to render on the display a view of a dataset, wherein a voxel visualized in the view has a value that is dependent upon a heterogeneity of the voxel at a sample location, the heterogeneity being calculated by taking a sum of a difference between a sampled voxel and its neighbor voxels, the voxel having a color that is a selected one of the multiple colors, the color being selected by using the value to perform a lookup into the color map;

wherein the view comprises multiple voxels, wherein the number of neighbor voxels used to determine the values of the voxels varies across the view.

7. A display method, comprising:

associating multiple colors in a color map to respective ranges of volumetric density measures;

receiving a volume dataset defining a volume; and rendering a view of a dataset, wherein a voxel visualized in the view has a value that is dependent upon a heterogeneity of the voxel at a sample location, the heterogeneity being calculated by taking a sum of a difference between a sampled voxel and its neighbor voxels;

the voxel having a color that is a selected one of the multiple colors, the color being selected by using the value to perform a lookup into the color map;

wherein the view comprises multiple voxels, wherein the number of neighbor voxels used to determine the values of the voxels varies across the view.

8. The method as described in claim 7 wherein the difference is measured in Hounsfield Units.

9. The method as described in claim 7 wherein the volumetric density measures are Hounsfield Units.

* * * * *